United States Patent
Neil et al.

(10) Patent No.: US 10,151,631 B2
(45) Date of Patent: Dec. 11, 2018

(54) SPECTROSCOPY WITH TAILORED SPECTRAL SAMPLING

(71) Applicant: KLA-Tencor Corporation, Milpitas, CA (US)

(72) Inventors: Mark A. Neil, San Jose, CA (US); Johannes D. de Veer, Menlo Park, CA (US)

(73) Assignee: KLA-Tencor Corporation, Milpitas, CA (US)

(*) Notice: Subject to any disclaimer, the term of this patent is extended or adjusted under 35 U.S.C. 154(b) by 0 days.

(21) Appl. No.: 15/644,571

(22) Filed: Jul. 7, 2017

(65) Prior Publication Data

US 2018/0094978 A1 Apr. 5, 2018

Related U.S. Application Data

(60) Provisional application No. 62/444,655, filed on Jan. 10, 2017, provisional application No. 62/403,708, filed on Oct. 4, 2016.

(51) Int. Cl.
*G01J 3/28* (2006.01)
*G01N 21/31* (2006.01)

(52) U.S. Cl.
CPC ............ *G01J 3/2803* (2013.01); *G01N 21/31* (2013.01)

(58) Field of Classification Search
CPC .... G01J 3/02; G01J 3/2803; G01J 3/28; G01J 3/45; G01J 4/00; G01N 21/00; G01N 21/31; G01B 9/02; G02B 27/44; G02B 27/42
See application file for complete search history.

(56) References Cited

U.S. PATENT DOCUMENTS

| | | |
|---|---|---|
| 5,856,871 A | 1/1999 | Cabib et al. |
| 6,288,781 B1 | 9/2001 | Lobb |
| 6,323,946 B1 | 11/2001 | Norton |
| 8,049,886 B1 | 11/2011 | Raksi |
| 8,107,073 B2 | 1/2012 | Norton et al. |
| 8,854,620 B2 | 10/2014 | Ho et al. |
| 9,395,241 B1 | 7/2016 | Choi |
| 2003/0071216 A1 | 4/2003 | Rabolt et al. |
| 2008/0204710 A1 | 8/2008 | Harrison et al. |

(Continued)

FOREIGN PATENT DOCUMENTS

| | | |
|---|---|---|
| JP | 2006071381 A | 3/2006 |
| JP | 2010223822 A | 10/2010 |

OTHER PUBLICATIONS

International Search Report dated Dec. 18, 2017 for PCT/US2017/054993.

*Primary Examiner* — Jamil Ahmed
(74) *Attorney, Agent, or Firm* — Suiter Swantz pc llo

(57) ABSTRACT

A spectrometer for tailored spectral sampling includes a dispersive element for spatially dispersing a spectrum of a light beam, a detector including a plurality of pixels distributed along a sampling direction, and a spectrum reshaping element including at least one of a reflective surface or a transmissive surface for reshaping the spatially-dispersed spectrum of the light beam from the dispersive element along the sampling direction to provide a selected distribution of the spectrum to the detector. The detector may spatially sample the spectrum of incident light with the plurality of pixels at selected spectral intervals based on the selected distribution of the spectrum.

25 Claims, 13 Drawing Sheets

(56) References Cited

U.S. PATENT DOCUMENTS

2010/0202055 A1* 8/2010 Norton .................... G01J 3/02
  359/568
2013/0077742 A1 3/2013 Schueler et al.

* cited by examiner

SPECTROSCOPY WITH TAILORED
SPECTRAL SAMPLING

CROSS-REFERENCE TO RELATED
APPLICATIONS

The present application claims the benefit under 35 U.S.C. § 119(e) of U.S. Provisional Application Ser. No. 62/403,708, filed Oct. 4, 2016, entitled SPECTROMETER WITH SIGNAL LINEAR IN ELECTRON VOLTS, naming Mark Allen Neil as inventor, which is incorporated herein by reference in the entirety.

The present application claims the benefit under 35 U.S.C. § 119(e) of U.S. Provisional Application Ser. No. 62/444,655, filed Jan. 10, 2017, entitled SPECTROMETER WITH SIGNAL LINEAR IN ELECTRON VOLTS, naming Mark Allen Neil and Johannes D. de Veer as inventors, which is incorporated herein by reference in the entirety.

TECHNICAL FIELD

The present invention relates generally to spectroscopy and, more particularly, to sampling spectroscopy signals linearly in photon energy.

BACKGROUND

Spectroscopy systems for measuring the spectral content of incident light may typically utilize a dispersive element such as a diffraction grating or a prism to spatially distribute the spectrum of the incident light onto a detector having an array of pixels. The incident spectrum may thus be sampled by the array of pixels according to the distribution of spectral components provided by the dispersion of the dispersive element. For example, a dispersion function may describe a spread of wavelengths per unit length across a detector of a spectroscopy system. Further, the distribution of spectral components of incident light on a detector of many spectroscopy systems may typically be approximately linear as a function of wavelength over a wavelength range of interest such that the pixels of the detector sample the incident spectrum at approximately uniform wavelength intervals. However, it may be the case that spectral sampling at approximately uniform wavelength intervals may not be well-suited for all spectral content of interest and that tailored spectral sampling may be desirable. It may therefore be desirable to provide a system and method for curing defects such as those identified above.

SUMMARY

A spectrometer is disclosed, in accordance with one or more illustrative embodiments of the present disclosure. In one illustrative embodiment, the spectrometer includes a dispersive element for spatially dispersing a spectrum of a light beam. In another illustrative embodiment, the spectrometer includes a detector including a plurality of pixels distributed along a sampling direction. In another illustrative embodiment, the detector spatially samples incident light with the plurality of pixels. In another illustrative embodiment, the spectrometer includes a spectrum reshaping element including at least one of a reflective surface or a transmissive surface for reshaping the spatially-dispersed spectrum of the light beam from the dispersive element along the sampling direction to provide a selected distribution of the spectrum to the detector. In another illustrative embodiment, the detector samples the spectrum at selected spectral intervals based on the selected distribution of the spectrum.

A metrology tool is disclosed, in accordance with one or more illustrative embodiments of the present disclosure. In one illustrative embodiment, the metrology tool includes an illumination source configured to illuminate an object. In another illustrative embodiment, the metrology tool includes a spectroscopy device. In another illustrative embodiment, the spectroscopy device includes a dispersive element for spatially dispersing a spectrum of a light beam emanating from the object in response to illumination from the illumination source. In another illustrative embodiment, the spectroscopy device includes a detector including a plurality of pixels distributed along a sampling direction. In another illustrative embodiment, the detector spatially samples incident light with the plurality of pixels. In another illustrative embodiment, the spectroscopy device includes a spectrum reshaping element including at least one of a reflective surface or a transmissive surface to reshape the spatially-dispersed spectrum of the light beam from the dispersive element along the sampling direction to provide a selected distribution of the spectrum to the detector. In another illustrative embodiment, the detector samples the spectrum at selected spectral intervals based on the selected distribution of the spectrum. In another illustrative embodiment, the metrology tool includes a controller communicatively coupled to the spectroscopy device to perform one or metrology measurements of the object based on the spectrum sampled by the detector.

A method is disclosed in accordance with one or more illustrative embodiments of the present disclosure. In one illustrative embodiment, the method includes generating, with a dispersive element, a spatially-dispersed spectrum of a light beam. In another illustrative embodiment, the method includes, reshaping, with at least one of a reflective surface or a transmissive surface, the spatially-dispersed spectrum of the light beam to provide a selected distribution of the spectrum to a detector. In another illustrative embodiment, the method includes sampling, with the detector, the spectrum at selected spectral intervals based on the selected distribution of the spectrum.

The accompanying drawings, which are incorporated in and constitute a part of the specification, illustrate embodiments of the invention and together with the general description, serve to explain the principles of the invention.

BRIEF DESCRIPTION OF DRAWINGS

The numerous advantages of the disclosure may be better understood by those skilled in the art by reference to the accompanying figures in which.

DETAILED DESCRIPTION

Figure 1A:
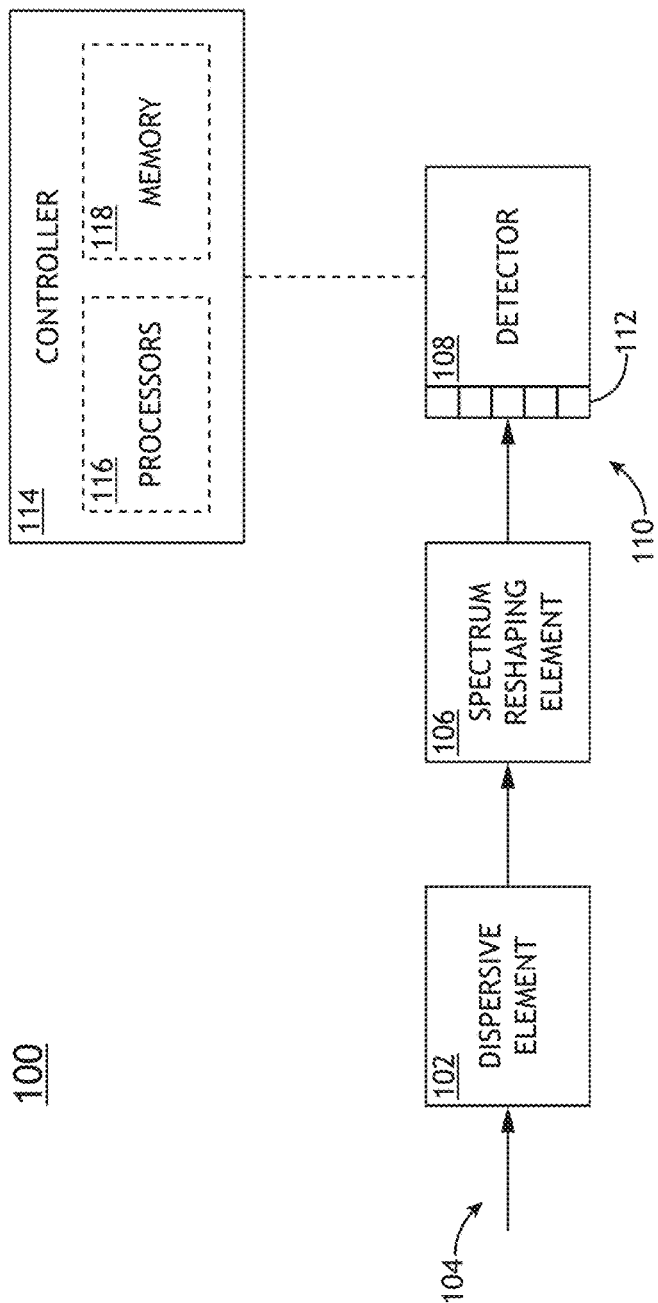
FIG. 1A is a conceptual view illustrating a spectroscopy system, in accordance with one or more embodiments of the present disclosure.

Reference will now be made in detail to the subject matter disclosed, which is illustrated in the accompanying drawings. The present disclosure has been particularly shown and described with respect to certain embodiments and specific features thereof. The embodiments set forth herein are taken to be illustrative rather than limiting. It should be readily apparent to those of ordinary skill in the art that various changes and modifications in form and detail may be made without departing from the spirit and scope of the disclosure.

Embodiments of the present disclosure are directed to systems and methods for spectroscopy with tailored spectral sampling. Spectroscopy systems may directly measure the spectrum of an illumination source (e.g. a laser source, a lamp source, a remote object, or the like) or may characterize the properties of a sample by measuring how the sample modifies the spectral content of illumination with a known spectral distribution. Further, it is often desirable to simultaneously measure the relative intensities of spectral components of a light signal of interest. Many typical spectroscopy systems for simultaneous measurement of spectral intensity across a spectral range include at least a dispersive element such as a diffraction grating or a prism to spatially disperse a spectrum of incident light and a detector having an array of pixels for sampling the spatially-dispersed spectrum. Accordingly, different spectral components (e.g. wavelengths or photon energies) of the incident light may propagate along different spatial paths to the detector. In this regard, spectral sampling may depend on the spatial distribution of the spectrum across the detector as well as the size and separation of pixels of the detector. Embodiments of the present disclosure are directed to tailoring the spatial distribution of spectral components on a detector to provide tailored spectral sampling.

The spatial distribution of the spectrum of light across a detector in a spectroscopy system may typically be characterized by a dispersion function (e.g. a linear dispersion, or the like) describing the spatial spread of spectral components (e.g. wavelength) per unit length on the detector. For example, the dispersion function may be, but is not required to be, written as $d\lambda/dx$, where $\lambda$ is the wavelength of incident light and x represents a direction across the detector. In a general sense, the value of the dispersion function of a spectroscopy system may vary as a function of wavelength such that $d\lambda/dx=F(\lambda)$. However, in many spectroscopy systems, the dispersion function varies slowly as a function of wavelength across a spectral range of interest. Accordingly, the spatial distribution of the spectrum of incident light on the detector may be approximately linear as a function of wavelength over the spectral range of interest. For example, a calibration curve mapping pixel numbers of the detector to wavelength may typically be approximated by a linear function:

$$P = A \cdot \lambda + B \quad (1)$$

where A and B are transform coefficients. In this regard, higher-order transform coefficients may be sufficiently smaller than at least transform coefficient A such that the linear approximation of equation (1) may be accurate within a selected tolerance (e.g. a Pearson correlation coefficient r above a selected value, a coefficient of determination $R^2$ above a selected value, or the like). A detector having an array of uniformly spaced pixels may thus sample the spectrum of incident light at approximately uniform wavelength intervals.

Additional embodiments of the present disclosure are directed to tailoring the spectral sampling based on expected properties of input light to be analyzed. It may be the case that that a spectrum of input light to be analyzed (e.g. associated with a light source to be analyzed, associated with interaction of light with an object to be analyzed, or the like) may include oscillations having a frequency that varies as a function of wavelength. Accordingly, sampling the spectrum at approximately uniform wavelength intervals may undersample some spectral ranges leading to aliasing errors and oversample other spectral ranges. It may thus be desirable to tailor the sampling intervals to avoid aliasing errors.

For example, the reflection coefficient of a film stack at an interface (k, k−1) having layers $k_1 \ldots k_n$ on a substrate $k_0$ may be written as:

$$\tilde{r}_k^s = \frac{r_{k,k-1}^s + \tilde{r}_{k-1}^s e^{-2i\beta_{k-1}}}{1 + r_{k,k-1}^s \tilde{r}_{k-1}^s e^{-2i\beta_{k-1}}}, \text{ and} \quad (2)$$

$$\tilde{r}_k^p = \frac{r_{k,k-1}^p + \tilde{r}_{k-1}^p e^{-2i\beta_{k-1}}}{1 + r_{k,k-1}^p \tilde{r}_{k-1}^p e^{-2i\beta_{k-1}}} \text{ with} \quad (3)$$

-continued $$\beta_{k-1} = \frac{2\pi}{\lambda}d_{k-1}n_{k-1}\cos\theta_{k-1} = \qquad (4)$$

$$\frac{2\pi v}{c}d_{k-1}n_{k-1}\cos\theta_{k-1} = \frac{2\pi E_p}{hc}d_{k-1}n_{k-1}\cos\theta_{k-1}, \text{ and}$$

$$E_p = \frac{hc}{\lambda} = hv \qquad (5)$$

for s and p polarizations, respectively, where $r_{k,k-1}$ is the reflection coefficient at the interface (k, k−1), $\tilde{r}_{k-1}$ is the reflectance from the layer below (k−1), $\lambda$ is the wavelength of light, $v$ the optical frequency of light, c is the speed of light, $E_p$ is the photon energy, h is Planck's constant, $d_k$ is the thickness of layer k, $n_k$ is the refractive index of layer k, and $\theta_k$ is the angle at which light with wavelength $\lambda$ propagates through the film layer k with respect to a surface normal of the film layer. The reflection coefficient at the interface (k, k−1) may be written for s and p polarized light as $$r^s_{k,k-1} = \frac{n_k\cos\theta_k - n_{k-1}\cos\theta_{k-1}}{n_k\cos\theta_k + n_{k-1}\cos\theta_{k-1}}, \text{ and} \qquad (6)$$

$$r^p_{k,k-1} = \frac{n_{k-1}\cos\theta_k - n_k\cos\theta_{k-1}}{n_{k-1}\cos\theta_k + n_k\cos\theta_{k-1}} \qquad (7)$$

respectively. Further, the reflectance of the film layer (e.g. corresponding to the reflected intensity of incident light) may be written as the squared modules of the reflection coefficient:

$$\mathcal{R} = |\tilde{r}_k|^2. \qquad (8)$$

Equations (2) through (8) indicate that the reflection coefficient of a film $\tilde{r}_k$ may contain oscillations with an oscillation frequency that is inversely proportional to the wavelength $\lambda$ of incident light but linearly proportional to the photon energy $E_p$ of the incident light (as well as the optical frequency $v$). A spectroscopy signal associated with a broadband illumination source reflected off the film may thus exhibit corresponding spectral oscillations. Accordingly, a spectroscopy system that samples the spectrum of incident light at approximately uniform wavelength intervals may provide non-uniform sampling of the spectral oscillations across a selected spectral range. For example, spectral oscillations associated with lower wavelengths may be undersampled leading to aliasing effects, while spectral oscillations at higher wavelengths may have more samples than required for a given application. Further, the impact of the non-uniform sampling of spectral oscillations may be particularly significant for, but not limited to, thick films (e.g. films having a thickness greater than approximately 3 microns) or for film stacks having a large number of layers (e.g. greater than 50 layers).

It is recognized herein that providing uniform sampling of spectral oscillations across a selected spectral range (e.g. providing an approximately constant number of samples per spectral oscillation) may be particularly beneficial for signal analysis techniques utilizing Fourier Transforms of a measured spectrum. While a measured spectrum may be post-processed in an attempt to mitigate undersampling or aliasing effects, such post-processing techniques may require significant processing time that may negatively impact throughput. Further, post-processing techniques may not be able to fully recover severely undersampled or aliased spectral data.

Additional embodiments of the present disclosure are directed to sampling the spectrum of incident light at approximately uniform intervals as a function of photon energy $E_p$. Accordingly, a calibration curve mapping pixel numbers of the detector to optical frequency may typically be approximated by a linear function:

$$P = C \cdot E_p + D \qquad (9)$$

where C and D are transform coefficients. In this regard, a spectroscopy system providing spectral sampling at approximately uniform photon energy intervals may provide approximately uniform sampling of spectral oscillations that have an oscillation frequency that varies linearly with photon energy. Further, the photon energy is linearly proportional to the optical frequency as indicated by Equation (5) such that sampling at approximately uniform intervals as a function of photon energy provides sampling at approximately uniform intervals as a function of optical frequency.

Additional embodiments of the present disclosure are directed to tailoring the spectral sampling of incident light (e.g. the intervals between adjacent sampled spectral components) based on expected properties of the spectrum of incident light. The spectral sampling of incident light may be tailored to provide any desired sampling pattern of incident light based on expected properties of the incident light.

Additional embodiments of the present disclosure are directed to a spectrum reshaping element for reshaping a spatially-dispersed spectrum from a dispersive element and directing a tailored (e.g. reshaped) spatial distribution of the spectrum to a detector. In this regard, a detector having an array of pixels with a known distribution may provide tailored spectral sampling of the spectrum of the incident light. For example, the spectrum reshaping element may include one or more reflective or refractive elements having tailored surfaces (e.g. any combination of one or more concave portions and/or one or more convex portions) to modify the dispersion function of a dispersive element to provide any tailored spatial distribution of spectral components on the detector.

Additional embodiments of the present disclosure are directed to systems and methods for spectroscopy with at least one optical element for reshaping a spatially-dispersed spectrum from a dispersive element and directing a tailored spatial distribution of the spectrum to a detector.

Additional embodiments of the present disclosure are directed to metrology systems including a spectroscopy system providing tailored spectral sampling. For example, a spectroscopy system providing tailored spectral sampling may be included in any type of metrology system such as, but not limited to, ellipsometry systems, reflectometry systems, or interferometry systems. Further, metrology systems including tailored spectral sampling may provide any type of metrology measurement such as, but not limited to, film thickness measurements, film composition measurements, film refractive index measurements, overlay measurements between multiple layers, or dimension measurements (e.g. critical dimension measurements, or the like).

FIG. 1A is a conceptual view illustrating a spectroscopy system 100, in accordance with one or more embodiments of the present disclosure.

In one embodiment, the spectroscopy system 100 includes a dispersive element 102 to spatially disperse a spectrum of a light beam 104 entering the spectroscopy system 100 such that the spectrum of the light beam 104 is spatially distributed along different paths, a spectrum reshaping element 106 having one or more reflective or transmissive surfaces for reshaping the spatial distribution of the spectrum provided by the dispersive element 102, and a detector 108 having a pixel array 110 to collect and sample the reshaped spatial distribution of the spectrum of the light beam 104. The dispersive element 102 and the spectrum reshaping element 106 in combination may provide any desired dispersion function that may be defined either as a function of wavelength (e.g. the spread of wavelengths per unit length on the detector 108 for any range of wavelengths) or photon energy (e.g. the spread of photon energies per unit length on the detector 108 for any range of photon energies). Accordingly, the dispersive element 102 and the spectrum reshaping element 106 may provide any selected spatial distribution of spectral components of any light beam 104 to the detector 108 for spectral sampling.

The spectral sampling of the spectroscopy system 100 may be determined by the overlap of the selected (e.g. tailored) dispersion function and the physical geometry of the pixel array 110 of the detector 108. The pixel array 110 of the detector 108 may have any distribution of pixels 112 to collect and sample the spatially-dispersed spectrum of the light beam 104. Further, each pixel 112 may collect an incident portion of the spectrum of the light beam 104 (e.g. a range of wavelengths or a range of photon energies) and generate a signal indicative of the spectral intensity of the incident portion of the spectrum. In one embodiment, the pixels 112 of the detector 108 have a common size and shape and are periodically distributed in an array (e.g. a 1D array, a 2D array, or the like). In another embodiment, the size, shape, and/or distribution of pixels 112 of the detector 108 may be design parameters for tailoring the spectral sampling of an incident light beam 104.

Further, the pixel array 110 may have any profile. For example, the pixel array 110 may be flat such that the pixels 112 form a plane. By way of another example, the pixel array 110 may be curved. In this regard, a curved pixel array 110 may compensate for field curvature associated with imaging optics within the spectroscopy system 100. Further, the profile of the pixel array 110 may be a design parameter for tailoring the spectral sampling of an incident light beam 104.

The detector 108 may include any type of optical detector known in the art suitable for measuring illumination received from the sample 126. For example, a detector 108 may include, but is not limited to, a charge-couple device (CCD) detector, a complementary metal-oxide-semiconductor (CMOS) detector, a diode array, an array of photomultiplier tubes (PMTs), an array of avalanche photodiodes (APDs), or the like.

In another embodiment, the spectroscopy system 100 includes a controller 114 communicatively coupled to at least the detector 108. The controller 114 may be configured to receive data from the detector 108 including, but not limited to, data indicative of the sampled spectrum of the light beam 104. In another embodiment, the controller 114 includes one or more processors 116 configured to execute program instructions maintained on a memory medium 118. In this regard, the one or more processors 116 of the controller 114 may execute any of the various process steps described throughout the present disclosure.

The one or more processors 116 of a controller 114 may include any processing element known in the art. In this sense, the one or more processors 116 may include any microprocessor-type device configured to execute algorithms and/or instructions. In one embodiment, the one or more processors 116 may consist of a desktop computer, mainframe computer system, workstation, image computer, parallel processor, or any other computer system (e.g., networked computer) configured to execute a program configured to operate the spectroscopy system 100, as described throughout the present disclosure. It is further recognized that the term "processor" may be broadly defined to encompass any device having one or more processing elements, which execute program instructions from a non-transitory memory medium 118. Further, the steps described throughout the present disclosure may be carried out by a single controller 114 or, alternatively, multiple controllers. Additionally, the controller 114 may include one or more controllers housed in a common housing or within multiple housings. In this way, any controller or combination of controllers may be separately packaged as a module suitable for integration into spectroscopy system 100. Further, the controller 114 may analyze data received from the detector 108 and feed the data to additional components within the spectroscopy system 100 or external to the spectroscopy system 100.

The memory medium 118 may include any storage medium known in the art suitable for storing program instructions executable by the associated one or more processors 116. For example, the memory medium 118 may include a non-transitory memory medium. By way of another example, the memory medium 118 may include, but is not limited to, a read-only memory, a random access memory, a magnetic or optical memory device (e.g., disk), a magnetic tape, a solid state drive and the like. It is further noted that memory medium 118 may be housed in a common controller housing with the one or more processors 116. In one embodiment, the memory medium 118 may be located remotely with respect to the physical location of the one or more processors 116 and controller 114. For instance, the one or more processors 116 of controller 114 may access a remote memory (e.g., server), accessible through a network (e.g., internet, intranet and the like). Therefore, the above description should not be interpreted as a limitation on the present invention but merely an illustration.

The spectroscopy system 100 may accept any type of light beam 104 with any spectrum. For example, the light beam 104 may include light from an illumination source for spectral sampling. For instance, the light beam 104 may include, but is not required to include, light from a laser source or a lamp source. In another instance, the light beam 104 may include, but is not required to include, light generated by an object of interest (e.g. by luminescence, blackbody radiation, or the like). By way of another example, the light beam 104 may include light from an illumination source (e.g. an illumination source having a known spectrum) incident on an object of interest and directed to the spectroscopy system 100 for spectral sampling. Accordingly, the spectroscopy system 100 may provide a spectroscopic analysis of the object of interest.

In one embodiment, the spectroscopy system 100 is provided as a stand-alone instrument for sampling the spectrum of a light beam 104. For example, the dispersive element 102, the spectrum reshaping element 106, and the detector 108 may be provided in a common housing suitable for connection to controller 114. By way of another example, the dispersive element 102, the spectrum reshaping element 106, the detector 108, and the controller 114 may be provided in a common housing.

In another embodiment, the spectroscopy system 100 may be incorporated into an external system. For example, the spectroscopy system 100 may be incorporated into a metrology system for characterizing one or more aspects of an object of interest based at least in part on tailored spectral sampling a light beam 104 from an object of interest.

A spectroscopy system 100 may be incorporated into any type of metrology system known in the art suitable for characterizing an object of interest at least in part through tailored spectral sampling. For example, metrology systems providing tailored spectral sampling may include, but are not limited to ellipsometry systems (e.g. spectroscopic ellipsometry systems, single-angle ellipsometry systems, multi-angle ellipsometry systems, angle-resolved ellipsometry systems, or the like), reflectometry systems (e.g. spectroscopic reflectometry systems, single-angle reflectometry systems, multi-angle reflectometry systems, angle-resolved reflectometry systems, or the like), or differential metrology systems (e.g. interferometry systems, or the like). Further, metrology systems incorporating tailored spectral sampling may be utilized to generate any type of metrology measurement known in the art based on spectroscopy with tailored spectral sampling such as, but not limited to, film thickness measurements, film composition measurements, film refractive index measurements, overlay measurements between multiple layers, or dimension measurements (e.g. critical dimension measurements, or the like).

Figure 1B:
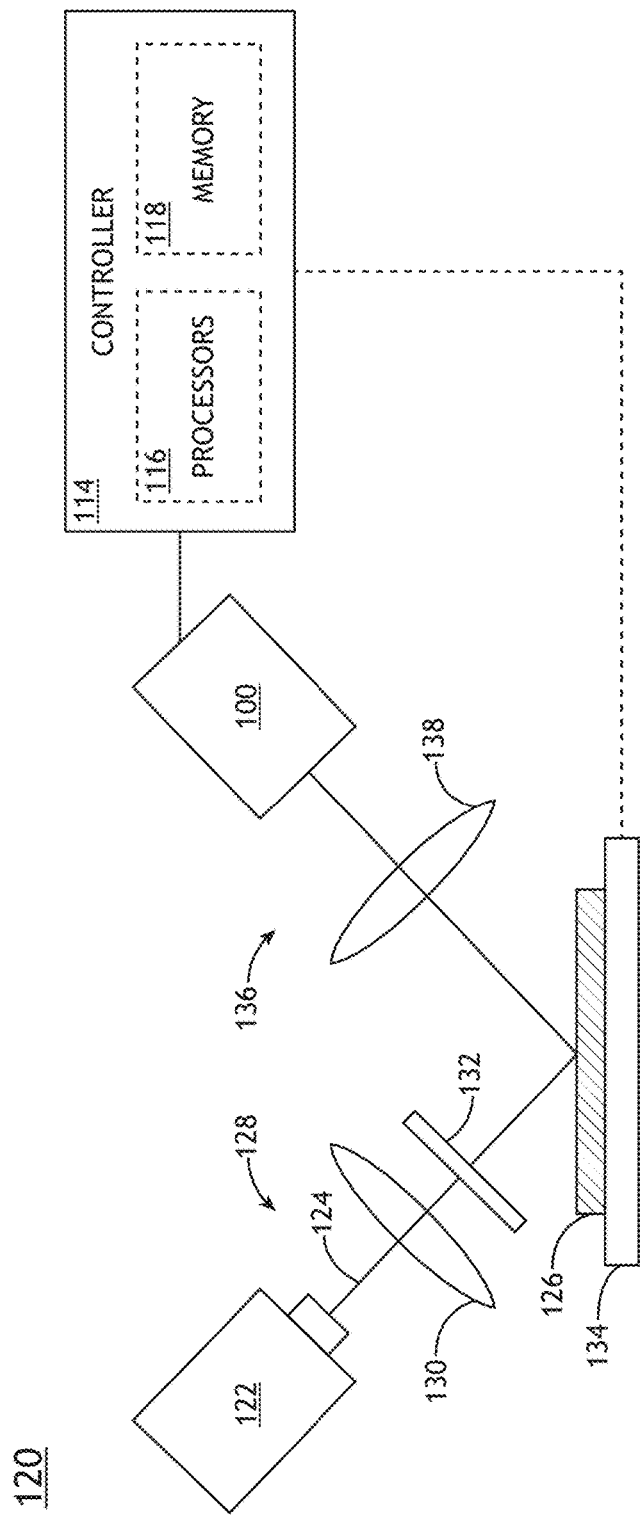
FIG. 1B is a conceptual view illustrating a metrology system providing tailored spectral sampling, in accordance with one or more embodiments of the present disclosure.

FIG. 1B is a conceptual view illustrating a metrology system 120 providing tailored spectral sampling, in accordance with one or more embodiments of the present disclosure.

In one embodiment, the metrology system 120 includes a metrology illumination source 122 to generate a metrology illumination beam 124. The metrology illumination beam 124 may include one or more selected wavelengths of light including, but not limited to, ultraviolet (UV) radiation, visible radiation, or infrared (IR) radiation.

In another embodiment, the metrology illumination source 122 directs the metrology illumination beam 124 to a sample 126 (e.g. an object of interest) via an illumination pathway 128. The illumination pathway 128 may include one or more lenses 130 or additional optical components 132 suitable for modifying and/or conditioning the metrology illumination beam 124. For example, the one or more optical components 132 may include, but are not limited to, one or more polarizers, one or more filters, one or more beam splitters, one or more diffusers, one or more homogenizers, one or more apodizers, or one or more beam shapers.

In another embodiment, the sample 126 is disposed on a sample stage 134. The sample stage 134 may include any device suitable for positioning the sample 126 within the metrology system 120. For example, the sample stage 134 may include any combination of linear translation stages, rotational stages, tip/tilt stages or the like.

In another embodiment, the metrology system 120 includes a spectroscopy system 100 configured to capture radiation emanating from the sample 126 through a collection pathway 136. For example, the spectroscopy system 100 may receive radiation reflected or scattered (e.g. via specular reflection, diffuse reflection, and the like) from the sample 126. By way of another example, the spectroscopy system 100 may receive radiation generated by the sample 126 (e.g. luminescence associated with absorption of the metrology illumination beam 124, or the like). By way of another example, the spectroscopy system 100 may receive one or more diffracted orders of radiation from the sample 126 (e.g. 0-order diffraction, ±1 order diffraction, ±2 order diffraction, and the like).

The collection pathway 136 may further include any number of optical elements to direct and/or modify radiation emanating from the sample 126 including, but not limited to one or more lenses 138, one or more filters, one or more polarizers, or one or more beam blocks.

Further, the metrology system 120 depicted in FIG. 1B may facilitate multi-angle illumination of the sample 126, and/or more than one metrology illumination source 122. In this regard, the metrology system 120 depicted in FIG. 1B may perform multiple metrology measurements. In another embodiment, one or more optical components may be mounted to a rotatable arm (not shown) pivoting around the sample 126 such that the angle of incidence of the metrology illumination beam 124 on the sample 126 may be controlled by the position of the rotatable arm.

In another embodiment, the controller 114 is communicatively coupled to the metrology illumination source 122 and/or elements of the illumination pathway 128 to direct the adjustment of the angle of incidence between the metrology illumination beam 124 and the sample 126. In another embodiment, the controller 114 directs the metrology illumination source 122 to provide one or more selected wavelengths of illumination (e.g. in response to feedback). In a general sense, the controller 114 may be communicatively coupled with any element within the metrology system 120.

Figure 2:
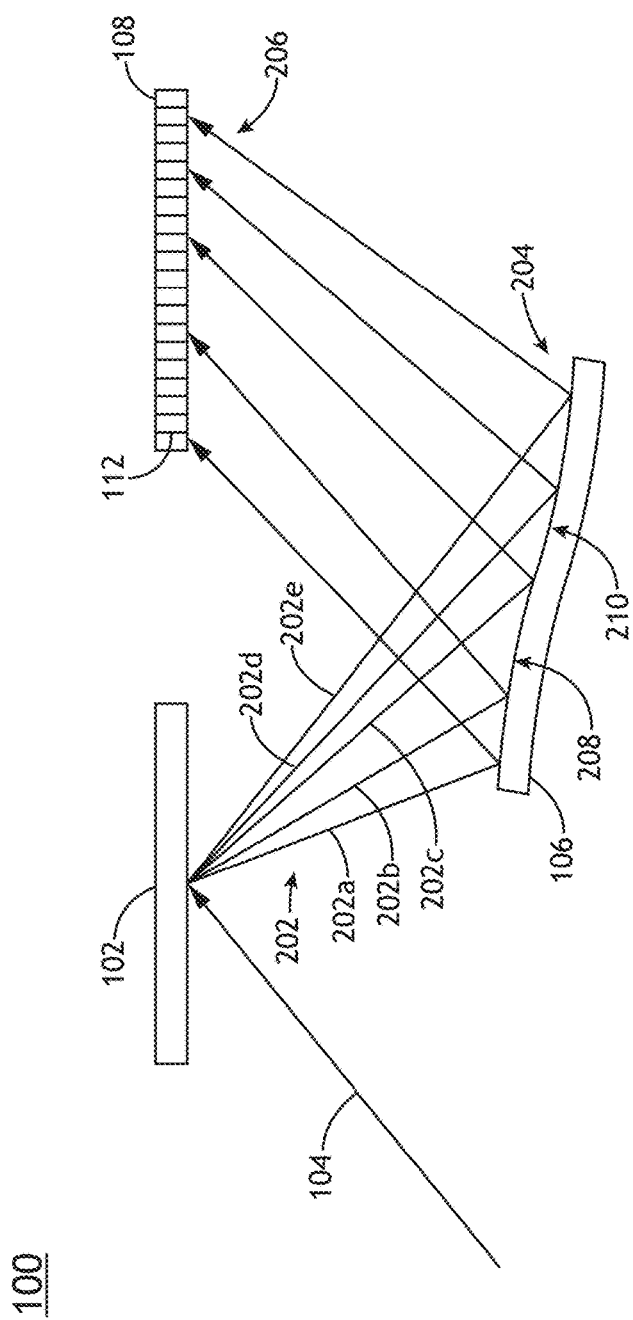
FIG. 2 is a conceptual view of a spectroscopy system, in accordance with one or more embodiments of the present disclosure.

FIG. 2 is a conceptual view of a spectroscopy system 100, in accordance with one or more embodiments of the present disclosure. In one embodiment, the spectroscopy system 100 includes a dispersive element 102 to receive and spatially disperse a spectrum of a light beam 104 such that various spectral components 202 of the light beam 104 are spatially distributed and a spectrum reshaping element 106 to reshape the spatial distribution of the spectral components 202 on a detector 108 to provide tailored spatial sampling of the light beam 104 by the pixel array 110 of the detector 108.

The dispersive element 102 may include any type of element known in the art suitable for spatially dispersing the spectrum of an incident light beam 104. In one embodiment, the dispersive element 102 includes one or more refractive elements such as, but not limited to, one or more prisms. In this regard, the dispersive element 102 may spatially disperse the spectrum of an incident light beam 104 based on differences in refracted angles at interfaces of the one or more refractive elements such that different spectral components (e.g. wavelengths or photon energies) may propagate along different spatial paths.

In another embodiment, as illustrated in FIG. 2, the dispersive element 102 includes one or more diffractive elements such as, but not limited to, one or more diffraction gratings. In this regard, the dispersive element 102 may spatially disperse the spectrum of an incident light beam 104 through diffraction into one or more diffraction orders. The one or more diffraction gratings of the dispersive element 102 may be any type of diffraction gratings known in the art such as, but not limited to, ruled gratings or holographic gratings. The one or more diffraction gratings may additionally be blazed to provide high diffraction efficiency for a particular wavelength or set of wavelengths.

The spectrum reshaping element 106 may include any type of element known in the art for reshaping the spatially-dispersed light beam 104 (e.g. reshaping the spatial distribution of the spectrum of the light beam 104) to provide a tailored dispersion at the detector 108. For example, the spectrum reshaping element 106 may reshape the spatial distribution of the spectrum of the light beam 104 by at least one reflective or transmissive surface with a tailored spatial profile designed to modify the optical paths of various spectral components of the light beam 104. By way of another example, the spectrum reshaping element 106 may include one or more surfaces to spatially disperse at least a portion of the spectrum of the light beam 104 in a different direction (e.g. an opposite direction) than provided by the dispersive element 102. In this regard, the spatial spread of spectral components per unit length (e.g. the dispersion function of the combined dispersive element 102 and spectrum reshaping element 106) may be tailored for all spectral components within a selected spectral range.

Further, the dispersive element 102 and the spectrum reshaping element 106 may be provided as any number of physical components within the spectroscopy system 100.

In one embodiment, the dispersive element 102 and the spectrum reshaping element 106 are provided as a single physical component. For example, the dispersive element 102 and the spectrum reshaping element 106 may be, but are not required to be, provided as a curved diffraction grating with a tailored spatial profile such that the dispersion function of the curved diffraction grating may be tailored. In this regard, the curved diffraction grating may provide a tailored spatial distribution of spectral components of the light beam 104 on the detector 108.

In another embodiment, as illustrated in FIG. 2, the dispersive element 102 and the spectrum reshaping element 106 are provided as separate physical components. In this regard, the spectral components 202 may have an incident spatial distribution 204 provided by the dispersive element 102 (e.g. spatial separation between various spectral components 202) and a tailored spatial distribution 206 provided by the combination of the dispersive element 102 and the spectrum reshaping element 106. Referring still to FIG. 2, spectrum reshaping element 106 may modify a received set of spatial separations of exemplary spectral components 202a-202e (e.g. associated with the incident spatial distribution 204) of the light beam 104 to provide a tailored set of spatial separations of the exemplary spectral components 202a-202e on the detector 108 (e.g. associated with the tailored spatial distribution 206).

The spectrum reshaping element 106 may include any number of reflective or refractive elements and/or surfaces to provide a tailored spectral distribution of a light beam 104 on the detector 108.

In one embodiment, as illustrated in FIG. 2, the spectrum reshaping element 106 includes a reflective element with a tailored surface profile to reshape the spatial distribution of spectral components 202 of the light beam 104 on the detector 108. For example, the spectrum reshaping element 106 may include any number of convex portions 208 and/or concave portions 210 designed to provide a tailored spatial distribution of spectral components 202 of the light beam 104 on the detector 108.

Figure 3:
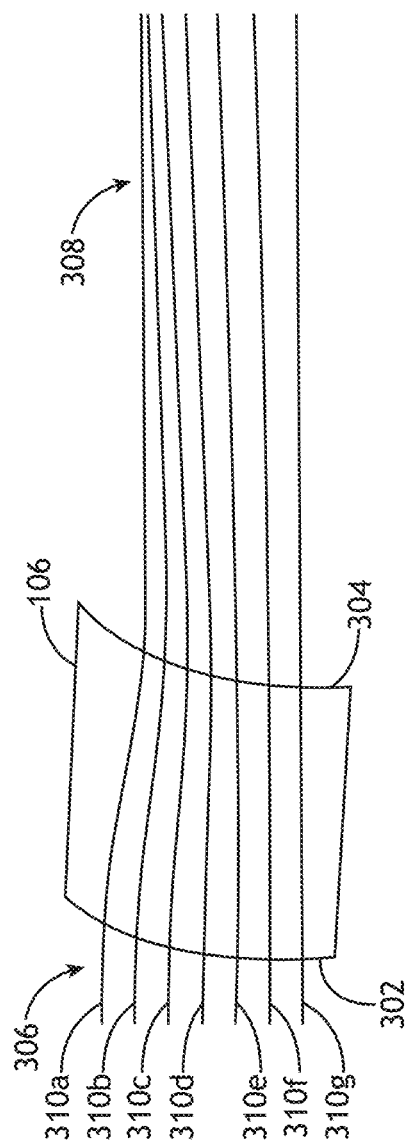
FIG. 3 is a schematic view of a refractive spectrum reshaping element, in accordance with one or more embodiments of the present disclosure.

In another embodiment, the spectrum reshaping element 106 includes a refractive element with one or more tailored surfaces to reshape the spatial distribution of spectral components 202 of the light beam 104 on the detector 108. FIG. 3 is a schematic view of a refractive spectrum reshaping element 106, in accordance with one or more embodiments of the present disclosure. In one embodiment, the spectrum reshaping element 106 includes a first tailored surface 302 and a second tailored surface 304 to modify an incident spatial distribution of spectral elements 306 to provide a tailored spatial distribution of spectral elements 308. For example, as illustrated in FIG. 3, the incident spatial distribution of spectral elements 306 may include exemplary spectral components 310a-310g distributed at uniform wavelength intervals (e.g. linearly distributed with respect to wavelength), and the tailored spatial distribution of spectral elements 308 provided by the spectrum reshaping element 106 may include the exemplary spectral components 310a-310g distributed with non-uniform wavelength intervals (e.g. non-linearly distributed with respect to wavelength).

Further, the tailored spatial distribution of spectral elements 308 may be, but is not required to be, distributed linearly with respect to photon energy or optical frequency.

It is recognized herein that a wide variety of configurations of the spectroscopy system 100 may be possible to provide tailored spectral sampling. Accordingly, it is to be understood that the elements of the spectroscopy system 100 illustrated in FIGS. 1A-3 along with the associated descriptions are provided solely for illustrative purposes and should not be interpreted as limiting. In a general sense, the spectroscopy system 100 may include any configuration of a spectroscopy system suitable for providing tailored spectral sampling.

For example, the spectroscopy system 100 may be configured in an imaging configuration in which one or more optical elements in the spectroscopy system 100 generate an image of the light beam 104 at an entrance aperture (e.g. an entrance slit, or the like) at the detector 108. Further, the dispersive element 102 and the spectrum reshaping element 106 may spatially disperse the spectrum of the light beam 104 such that the image of the light beam 104 at the detector 108 is spectrally dispersed with a tailored dispersion function.

In one embodiment, the dispersive element 102 and/or the spectrum reshaping element 106 are designed (e.g. curved) to contribute to the formation of the spectrally-dispersed image of the entrance aperture on the detector 108. For example, surfaces of the dispersive element 102 and/or the spectrum reshaping element 106 may be designed to directly provide a spectrally-dispersed image of the entrance aperture with a tailored dispersion function on the detector 108. By way of another example, surfaces of the dispersive element 102 and/or the spectrum reshaping element 106 may be designed in combination with one or more additional optical elements (e.g. one or more lenses, curved mirrors, or the like) to provide a spectrally-dispersed image of the entrance aperture with a tailored dispersion function on the detector 108. Further, the spectroscopy system 100 may include folding mirrors to fold the optical path of the light beam 104 in any configuration.

The spectrum reshaping element 106, alone or in combination with at least the dispersive element 102, may provide any selected dispersion function to provide any selected spatial distribution of spectral components of the light beam 104 on the detector 108.

In one embodiment, the dispersion function of the spectrum reshaping element 106, alone or in combination with at least the dispersive element 102, is designed based on expected spectral properties of an incident light beam 104. For example, as previously described herein, some sources of light suitable for spectroscopy may include spectral oscillations (e.g. oscillations of spectral power as a function of wavelength) having an oscillation frequency that varies across different spectral bands. Accordingly, it may be desirable to design the spectroscopy system 100 to provide a tailored dispersion function based on the expected spectral properties to generate an approximately constant number of samples per spectral oscillation over a selected spectral range.

As previously described herein, it is to be understood for the purposes of the present disclosure that the term "approximately linear" may refer to a distribution that may be approximated with a linear function within a selected tolerance. Accordingly, a non-linear calibration function may be utilized to correct deviations of the tailored dispersion function from an ideal selected dispersion function.

In another embodiment, the dispersion function of the spectrum reshaping element 106, alone or in combination with at least the dispersive element 102, is designed to be approximately linear as a function of photon energy. In this regard, a detector 108 having a pixel array 110 with uniformly distributed pixels 112 may sample the spectrum of an incident light beam 104 at approximately uniform sample intervals as a function of photon energy.

As described previously herein in equations (2) through (8), the reflection coefficients of films may include spectral oscillations that vary linearly as a function of photon energy. Accordingly, a spectroscopy system 100 for providing approximately linear spectral sampling as a function of photon energy may provide an approximately constant number of samples per spectral oscillation over a selected spectral range.

FIGS. 4A through 4D provide a comparison between spectral sampling that is approximately linear as a function of wavelength and spectral sampling that is approximately linear as a function of photon energy for a 6 micron film.

Figure 4A:
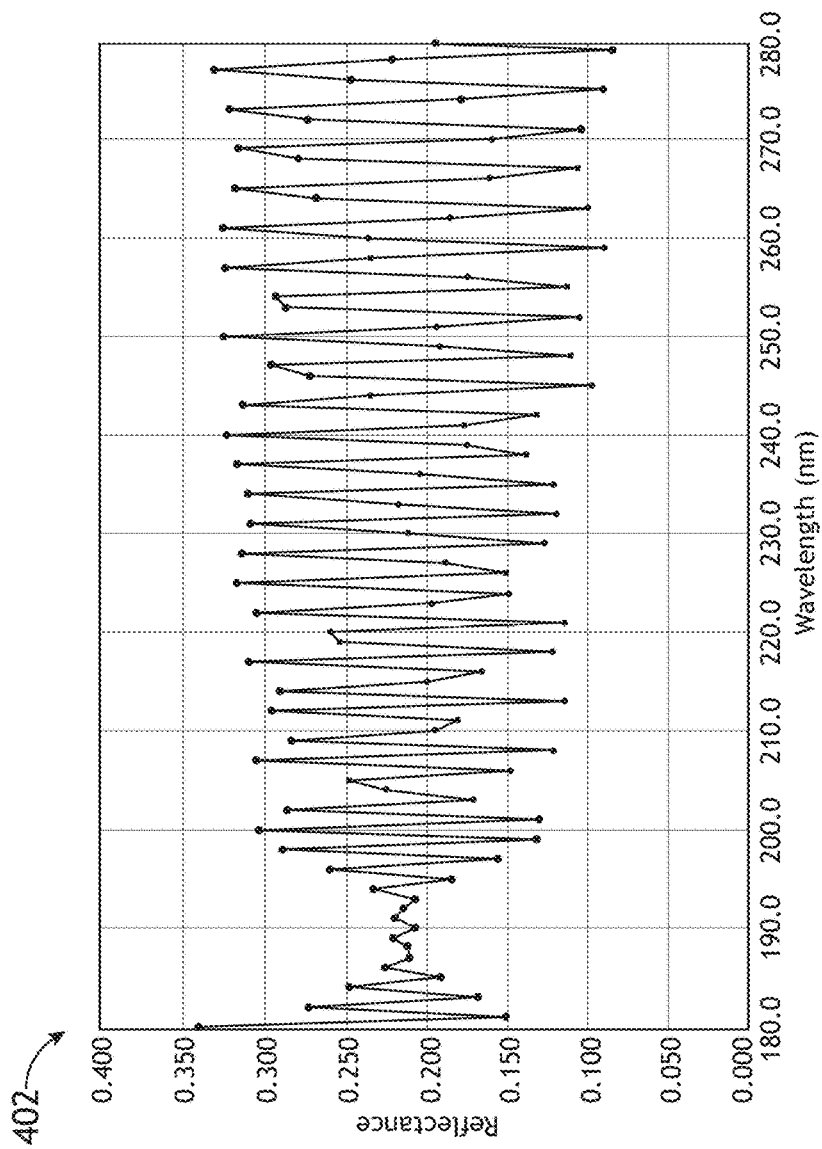
FIG. 4A is a plot of the simulated reflectance of a 6 micron film at a normal incidence angle sampled with a spectroscopy system providing approximately uniform sampling as a function of wavelength across a spectral range of approximately 180 nm to 280 nm, in accordance with one or more embodiments of the present disclosure.
Figure 4B:
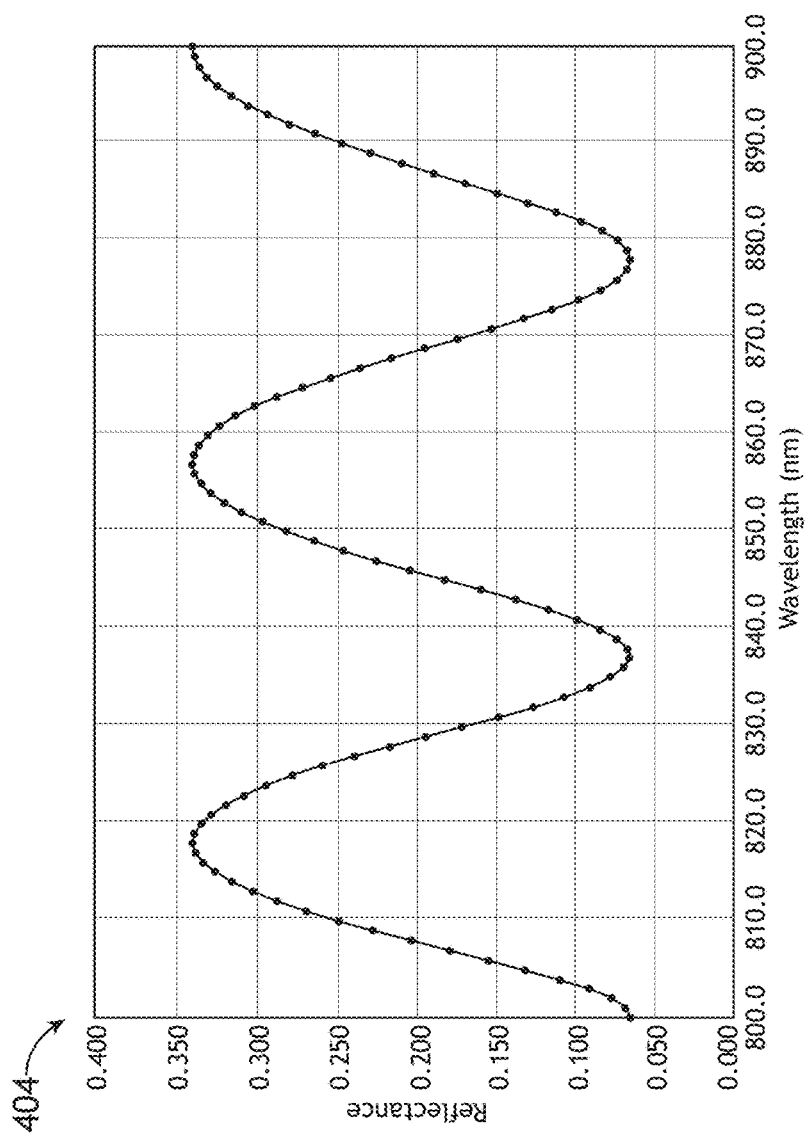
FIG. 4B is a plot of the simulated reflectance of the 6 micron film sampled with the same spectroscopy system as in FIG. 4A across a spectral range of approximately 800 nm to 900 nm, in accordance with one or more embodiments of the present disclosure.

FIG. 4A is a plot 402 of the simulated reflectance of a 6 micron film at a normal incidence angle sampled with a spectroscopy system 100 providing approximately uniform sampling as a function of wavelength across a spectral range of approximately 180 nm to 280 nm, in accordance with one or more embodiments of the present disclosure. FIG. 4B is a plot 404 of the simulated reflectance of the 6 micron film sampled with the same spectroscopy system 100 as in FIG. 4A across a spectral range of approximately 800 nm to 900 nm, in accordance with one or more embodiments of the present disclosure.

As illustrated by FIGS. 4A and 4B, a spectroscopy system 100 providing approximately uniform sampling as a function of wavelength may fail to adequately sample the spectrum across a desired spectral range. For example, as illustrated in FIG. 4A, the spectrum is undersampled with less than 2 samples per oscillation in the spectral range from 180 to 280 nm. However, as illustrated in FIG. 4B, the spectrum is sampled with approximately 40 samples per oscillation in the spectral range from 800 nm to 900 nm, which may include more samples than required to characterize the spectral properties across this spectral range. It is recognized herein that while oversampling may not be detrimental to the signal quality, it may reduce throughput.

Figure 4C:
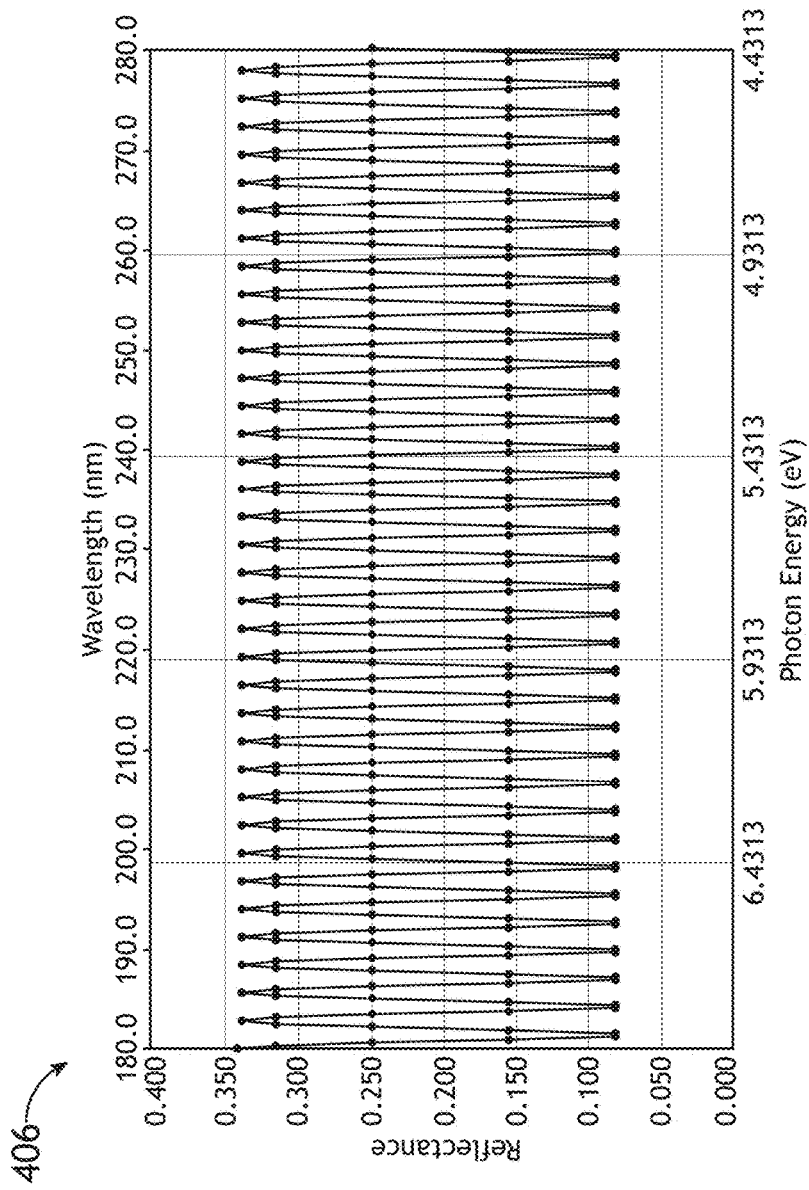
FIG. 4C is a plot of the simulated reflectance of the 6 micron film sampled with a spectroscopy system providing approximately uniform sampling as a function of photon energy across a spectral range of approximately 180 nm to 280 nm (6.9313 eV to 4.4313 eV), in accordance with one or more embodiments of the present disclosure.
Figure 4D:
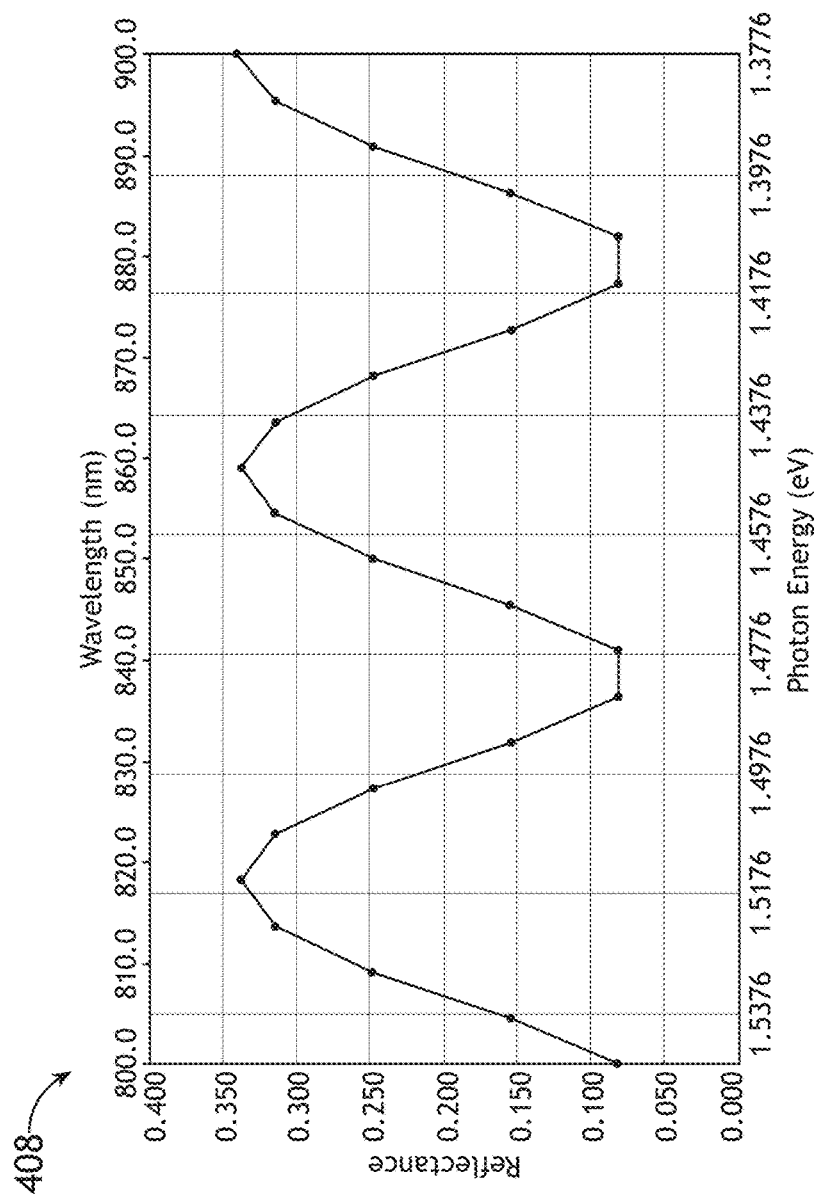
FIG. 4D is a plot of the simulated reflectance of the 6 micron film sampled with the same spectroscopy system as in FIG. 4C across a spectral range of approximately 800 nm to 900 nm (1.5376 eV to 1.3776 eV), in accordance with one or more embodiments of the present disclosure.

FIG. 4C is a plot 406 of the simulated reflectance of the 6 micron film sampled with a spectroscopy system 100 providing approximately uniform sampling as a function of photon energy across a spectral range of approximately 180 nm to 280 nm (6.9313 eV to 4.4313 eV), in accordance with one or more embodiments of the present disclosure. FIG. 4D is a plot 408 of the simulated reflectance of the 6 micron film sampled with the same spectroscopy system 100 as in FIG. 4C across a spectral range of approximately 800 nm to 900 nm (1.5376 eV to 1.3776 eV), in accordance with one or more embodiments of the present disclosure.

As illustrated by FIGS. 4C and 4D, a spectroscopy system 100 providing approximately uniform sampling as a function of wavelength may adequately sample the spectrum across a desired spectral range. For example, the spectrum is sampled with approximately 8 samples per oscillation across the entire selected spectral range.

FIGS. 5A through 5D provide a similar comparison between spectral sampling that is approximately linear as a function of wavelength and spectral sampling that is approximately linear as a function of photon energy for a 50-layer 3D flash memory stack including alternating layers of oxide and nitride layers of 350 Angstroms and 300 Angstroms, respectively.

Figure 5A:
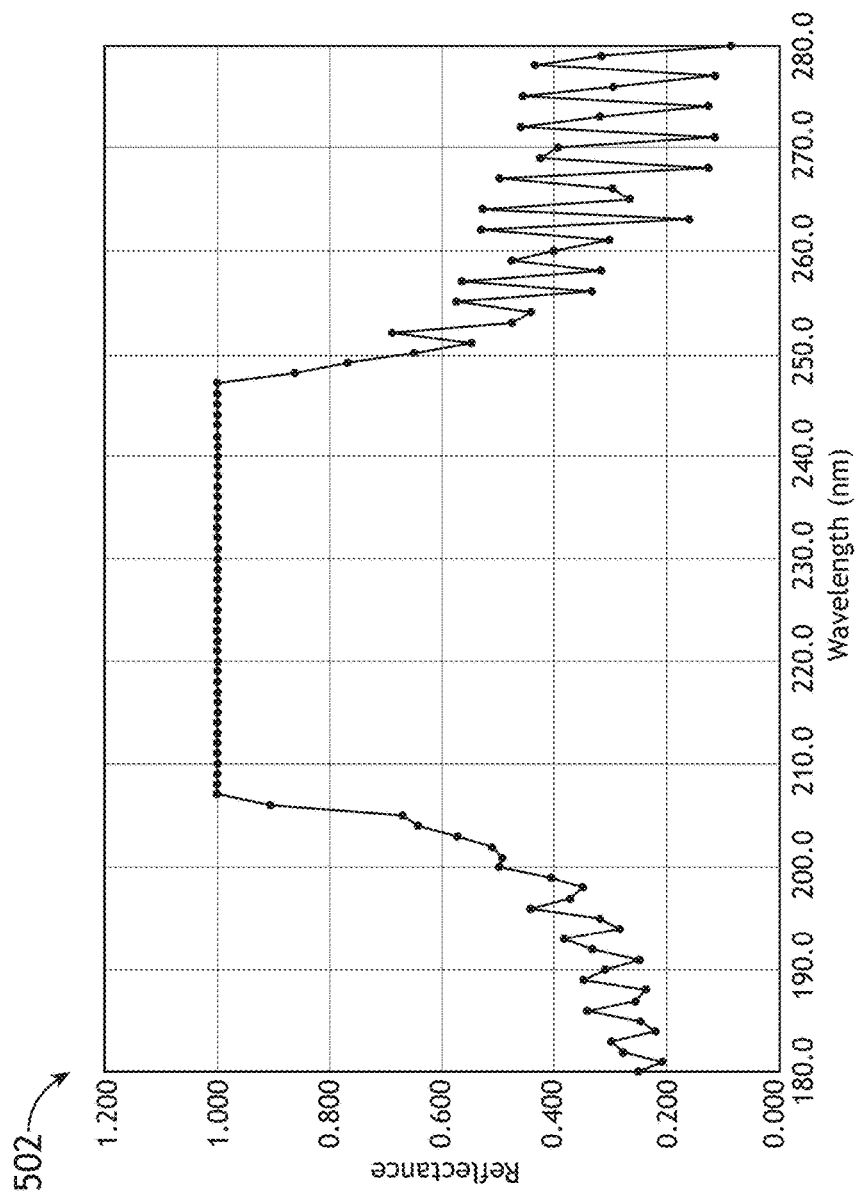
FIG. 5A is a plot 502 of the simulated reflectance of a 3D flash memory stack at a normal incidence angle sampled with a spectroscopy system providing approximately uniform sampling as a function of wavelength across a spectral range of 180 nm to 280 nm, in accordance with one or more embodiments of the present disclosure.
Figure 5B:
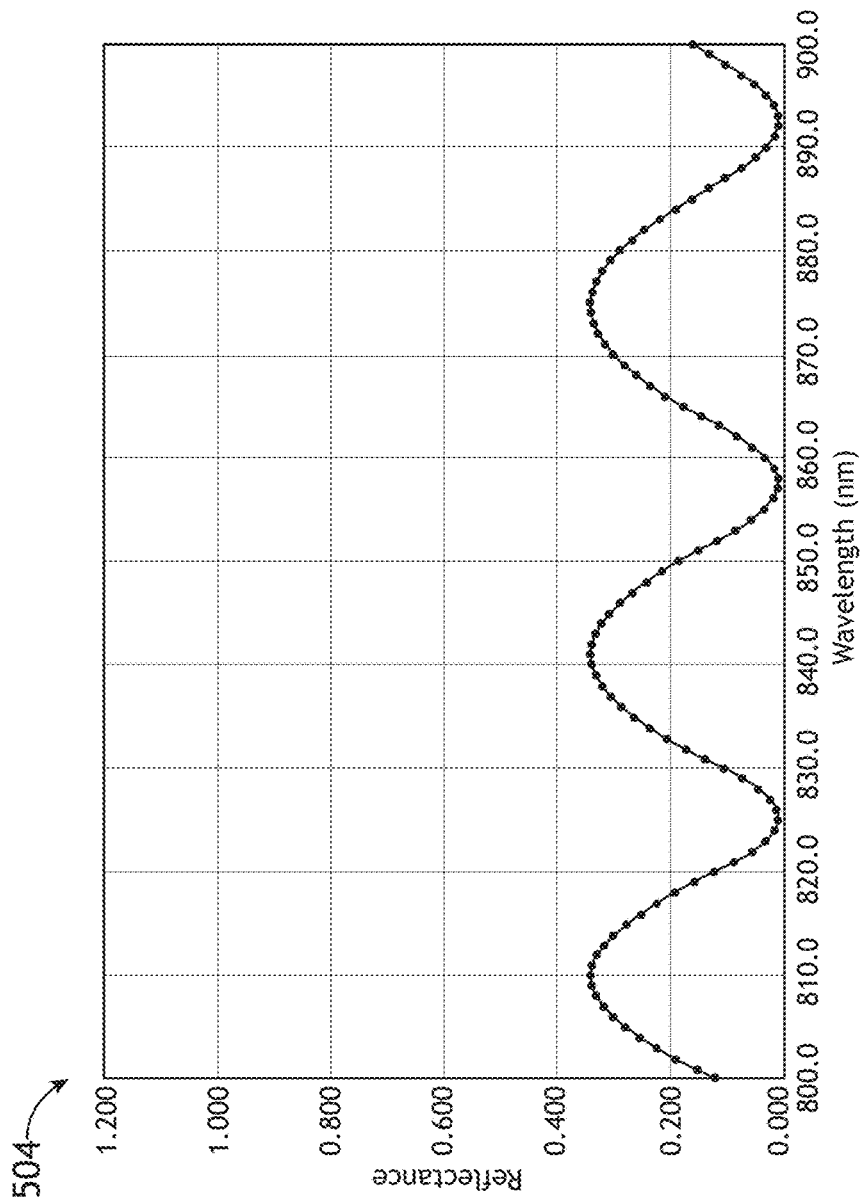
FIG. 5B is a plot of the simulated reflectance of the 3D flash memory stack sampled with the same spectroscopy system as in FIG. 5A across a spectral range of 800 nm to 900 nm, in accordance with one or more embodiments of the present disclosure.

FIG. 5A is a plot of the simulated reflectance of the 3D flash memory stack at a normal incidence angle sampled with a spectroscopy system 100 providing approximately uniform sampling as a function of wavelength across a spectral range of 180 nm to 280 nm, in accordance with one or more embodiments of the present disclosure. FIG. 5B is a plot 504 of the simulated reflectance of the 3D flash memory stack sampled with the same spectroscopy system 100 as in FIG. 5A across a spectral range of 800 nm to 900 nm, in accordance with one or more embodiments of the present disclosure.

As illustrated by FIGS. 5A and 5B, a spectroscopy system 100 providing approximately uniform sampling as a function of wavelength may fail to adequately sample the spectrum across a desired spectral range. For example, as illustrated in FIG. 5A, the spectrum is undersampled with less than 2 samples per oscillation in the spectral range from 180 to 280 nm. However, as illustrated in FIG. 5B, the spectrum is sampled with approximately 32 samples per oscillation in the spectral range from 800 nm to 900 nm.

Figure 5C:
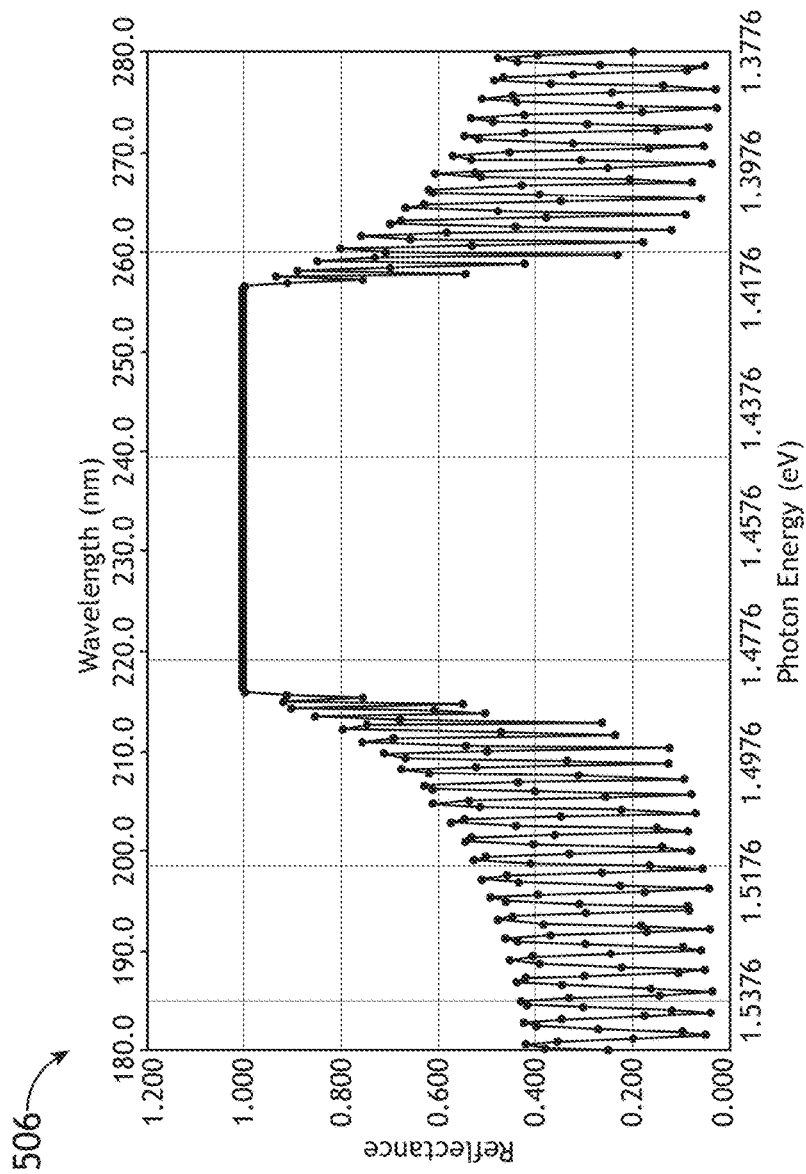
FIG. 5C is a plot of the simulated reflectance of the 3D flash memory stack sampled with a spectroscopy system providing approximately uniform sampling as a function of photon energy across a spectral range of 180 nm to 280 nm (6.9313 eV to 4.4313 eV), in accordance with one or more embodiments of the present disclosure.
Figure 5D:
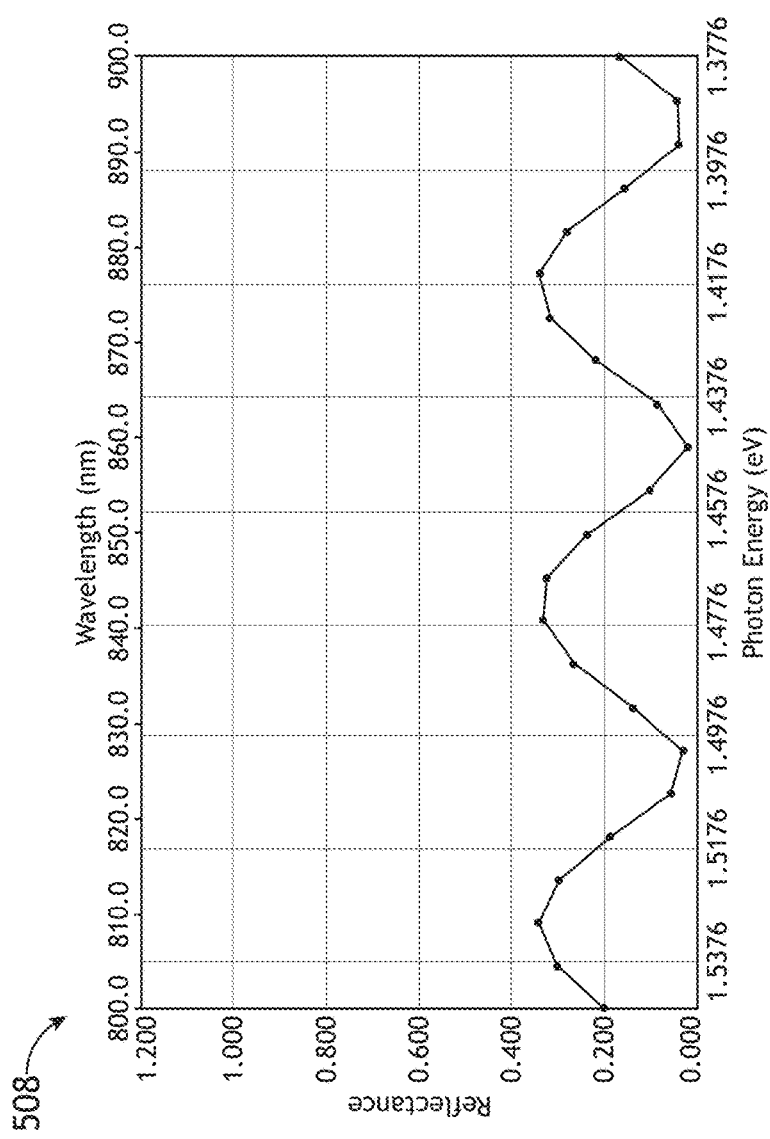
FIG. 5D is a plot of the simulated reflectance of the 3D flash memory stack sampled with the same spectroscopy system 100 as in FIG. 4C across a spectral range of 800 nm to 900 nm (1.5376 eV to 1.3776 eV), in accordance with one or more embodiments of the present disclosure.

FIG. 5C is a plot 506 of the simulated reflectance of the 3D flash memory stack sampled with a spectroscopy system 100 providing approximately uniform sampling as a function of photon energy across a spectral range of 180 nm to 280 nm (6.9313 eV to 4.4313 eV), in accordance with one or more embodiments of the present disclosure. FIG. 5D is a plot 508 of the simulated reflectance of the 3D flash memory stack sampled with the same spectroscopy system 100 as in FIG. 4C across a spectral range of 800 nm to 900 nm (1.5376 eV to 1.3776 eV), in accordance with one or more embodiments of the present disclosure.

As illustrated by FIGS. 5C and 5D, a spectroscopy system 100 providing approximately uniform sampling as a function of wavelength may adequately sample the spectrum across a desired spectral range. For example, the spectrum is sampled with approximately 8 samples per oscillation across the entire selected spectral range.

Figure 6:
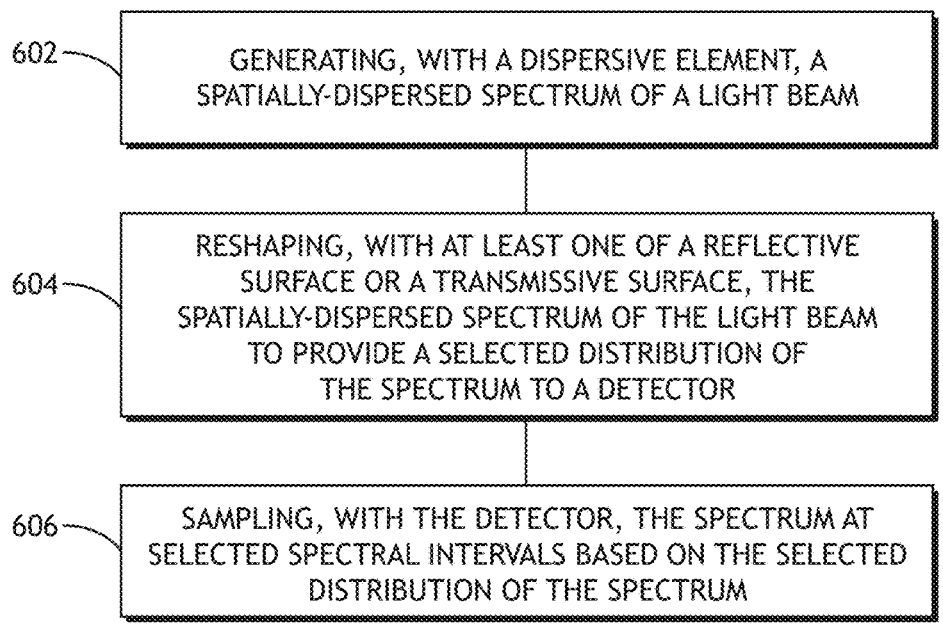
FIG. 6 is a flow diagram illustrating steps performed in a method for spectroscopy with tailored spectral sampling.

FIG. 6 is a flow diagram illustrating steps performed in a method 600 for spectroscopy with tailored spectral sampling. Applicant notes that the embodiments and enabling technologies described previously herein in the context of spectroscopy system 100 should be interpreted to extend to method 600. It is further noted, however, that the method 600 is not limited to the architecture of spectroscopy system 100.

In one embodiment, the method 600 includes a step 602 of generating, with a dispersive element, a spatially-dispersed spectrum of a light beam. In this regard, different spectral components of a spectrum of the incident light may propagate along different optical paths. A dispersive element for spatially-dispersing the incident light beam may include, but is not limited to, one or more diffraction gratings or one or more prisms.

In another embodiment, the method 600 includes a step 604 of reshaping, with at least one of a reflective surface or a transmissive surface, the spatially-dispersed spectrum of the light beam to provide a selected distribution of the spectrum to a detector. It is recognized herein that the dispersion function of a dispersive element (e.g. the spread of wavelength per unit length or unit angle as a function of wavelength) may be determined by the dispersion mechanism (e.g. diffraction, refraction, or the like).

It may be the case that the spatial distribution of the spectrum may not be suitable for a light beam of interest. For example, although the value of the dispersion function of a grating at one or more wavelengths may be tailored (e.g. by the pitch of the grating, or the like), the overall shape of the distribution function over a selected spectral range may be determined by the grating equation. In step 604, the spatially-dispersed spectrum from the dispersive element may be reshaped to provide a selected (e.g. tailored) spatial distribution of the spectrum to a detector. For example, a spectrum reshaping element including one or more reflective or transmissive surfaces may reshape the spectrally-dispersed light beam and thus tailor the spatial distribution of the spectrum on the detector.

The tailored spatial distribution of the spectrum may be selected based on expected properties of incident light beams of interest. For example, light beams of interest such as, but not limited to, thick films or multilayer film stacks, may exhibit spectral oscillations having an oscillation frequency that varies linearly with photon volts. Accordingly, in one instance, step 604 may include, but is not required to include, reshaping the spatially-dispersed light beam to provide a substantially linear distribution of the spectrum as a function of photon energy (or optical frequency) on the detector.

In another embodiment, the method 600 includes a step 606 of sampling, with the detector, the spectrum at selected spectral intervals based on the selected distribution of the spectrum. For example, a detector may include an array of pixels that define spatial intervals at which the detector may sample incident light. Further, each pixel may collect and sample incident portions of the spatially-dispersed spectrum. Accordingly, step 606 may include sampling the spectrum of the light beam according to the tailored spatial distribution of the spectrum provided by step 602 and step 604.

Returning to the previous example, in the case that step 602 and step 604 provide a substantially linear distribution of the spectrum as a function of photon energy (or optical frequency) on a detector having an array of uniformly distributed pixels, step 606 may include sampling the spectrum of the light beam at approximately uniform spectral intervals as a function of photon energy.

In a general sense, tailored spectral sampling may be provided by tailoring the overlap of the spatial distribution of the spectrum (e.g. in step 602 and step 604) and the pixel layout provided by the detector for sampling (e.g. in step 606).

The herein described subject matter sometimes illustrates different components contained within, or connected with, other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "connected", or "coupled", to each other to achieve the desired functionality, and any two components capable of being so associated can also be viewed as being "couplable", to each other to achieve the desired functionality. Specific examples of couplable include but are not limited to physically interactable and/or physically interacting components and/or wirelessly interactable and/or wirelessly interacting components and/or logically interactable and/or logically interacting components.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes. Furthermore, it is to be understood that the invention is defined by the appended claims.

What is claimed:

1. A spectrometer, comprising:
a dispersive element for spatially dispersing a spectrum of a light beam according to a first spatial distribution of spectral components;
a detector including a plurality of pixels distributed along a sampling direction, wherein the detector is configured to spatially sample incident light with the plurality of pixels; and
a spectrum reshaping element including at least one of a reflective surface or a transmissive surface having a surface profile that receives the spectral components of the light beam from the dispersive element at selected locations on the spectrum reshaping element based on the first spatial distribution and directs the spectral components along location-dependent paths to provide a second spatial distribution of spectral components along the sampling direction to the detector, wherein the second spatial distribution of spectral components at the detector provides a substantially linear relationship between photon energies of the spectral components and positions of the spectral components on the detector over a selected spectral range, wherein the detector samples the spectrum at substantially uniform intervals of photon energy.

2. The spectrometer of claim 1, wherein the plurality of pixels of the detector have a uniform size along the sampling direction, wherein the plurality of pixels of the detector sample the spectrum at uniform intervals of photon energy.

3. The spectrometer of claim 1, wherein the spectrum reshaping element provides a substantially constant number of samples for spectral oscillations of the light beam across the selected spectral range.

4. The spectrometer of claim 1, wherein the spectrum reshaping element includes two or more surfaces having spatial profiles selected to provide the second spatial distribution of spectral components to the detector based on the dispersion of the dispersive element.

5. The spectrometer of claim 4, wherein the spectrum reshaping element comprises:
a curved mirror, wherein a curvature of the curved mirror is selected to vary along the sampling direction to provide the second spatial distribution of spectral components to the detector based on the dispersion of the dispersive element.

6. The spectrometer of claim 5, wherein a first portion of a reflective surface of the curved mirror is concave and a second portion of the reflective surface is convex.

7. The spectrometer of claim 4, wherein the spectrum reshaping element comprises:
a refractive optical element, wherein a curvature of at least one surface of the refractive optical element is selected to vary along the sampling direction to provide the second spatial distribution of spectral components to the detector based on the known dispersion of the dispersive element.

8. The spectrometer of claim 1, wherein the dispersive element comprises:
at least one of a diffraction grating or a prism.

9. The spectrometer of claim 1, wherein the dispersive element and the spectrum reshaping element are formed from a single component to simultaneously spatially disperse the spectrum of the light beam and provide the second spatial distribution of spectral components to the detector.

10. A metrology tool, comprising:
an illumination source configured to illuminate an object;
a spectroscopy device comprising:
a dispersive element for spatially dispersing a spectrum of a light beam emanating from the object in response to illumination from the illumination source according to a first spatial distribution of spectral components;
a detector including a plurality of pixels distributed along a sampling direction, wherein the detector is configured to spatially sample incident light with the plurality of pixels; and
a spectrum reshaping element including at least one of a reflective surface or a transmissive surface having a surface profile tailored, based on a dispersion of the dispersive element, to receive the first spatial distribution of spectral components from the dispersive element and provide a second spatial distribution of spectral components to the detector, wherein the second spatial distribution of spectral components at the detector provides a substantially linear relationship between photon energies of the spectral components and positions of the spectral components on the detector over a selected spectral range, wherein the detector samples the spectrum at substantially uniform intervals of photon energy; and
a controller communicatively coupled to the spectroscopy device, the controller including one or more processors configured to execute instructions configured to cause the one or more processors to perform one or metrology measurements of the object based on the spectrum sampled by the detector.

11. The metrology tool of claim 10, wherein the one or more metrology measurements comprise:
at least one of a thickness measurement of a film on the object, a composition measurement of a film on the object, a refractive index measurement of at least a portion of the object, an overlay measurement between multiple layers on the object, or a dimension measurement of a feature on the object.

12. The metrology tool of claim 10, wherein the illumination source comprises:
a broadband illumination source.

13. The metrology tool of claim 10, wherein the plurality of pixels of the detector have a uniform size along the sampling direction, wherein the plurality of pixels of the detector sample the spectrum of the light beam at uniform intervals of photon energy.

14. The metrology tool of claim 10, wherein the spectrum reshaping element provides a substantially constant number of samples for spectral oscillations of the light beam across the selected spectral range.

15. The metrology tool of claim 10, wherein the spectrum reshaping element includes two or more surfaces having spatial profiles selected to provide the second spatial distribution of spectral components to the detector based on the dispersion of the dispersive element.

16. The metrology tool of claim 15, wherein the spectrum reshaping element comprises:
a curved mirror, wherein a curvature of the curved mirror is selected to vary along the sampling direction to provide the second spatial distribution of spectral components to the detector based on the dispersion of the dispersive element.

17. The metrology tool of claim 16, wherein a first portion of a reflective surface of the curved mirror is concave and a second portion of the reflective surface is convex.

18. The metrology tool of claim 15, wherein the spectrum reshaping element comprises:
a refractive optical element, wherein a curvature of at least one surface of the refractive optical element is selected to vary along the sampling direction to provide the second spatial distribution of spectral components to the detector based on the known dispersion of the dispersive element.

19. The metrology tool of claim 10, wherein the dispersive element comprises:
at least one of a diffraction grating or a prism.

20. The metrology tool of claim 10, wherein the dispersive element and the spectrum reshaping element are formed from a single component to simultaneously spatially disperse the spectrum of the light beam and provide the second spatial distribution of spectral components to the detector.

21. A method, comprising:
generating, with a dispersive element, a spatially-dispersed spectrum of a light beam according to a first spatial distribution of spectral components;
reshaping, with at least one of a reflective surface or a transmissive surface having a surface profile tailored to receive the spectral components of the light, based on the first spatial distribution of spectral components and direct the spectral components along location-dependent paths to provide a second spatial distribution of spectral components to a detector, wherein the second spatial distribution of spectral components at the detector provides a substantially linear relationship between photon energies of the spectral components and positions of the spectral components on the detector over a selected spectral range; and
sampling, with the detector, the spectrum at substantially uniform intervals of photon energy.

22. The method of claim 21, wherein sampling the spectrum at intervals of photon energy based on an overlap between the second spatial distribution of spectral components and a distribution of pixels of the detector comprises:
sampling the spectrum at uniform intervals of photon energy.

23. The method of claim 22, wherein the spectrum reshaping element provides a substantially constant number of samples for spectral oscillations in the spectrum of the light beam across the selected spectral range.

24. The method of claim 21, further comprising:
performing one or metrology measurements of the object based on the spectrum sampled by the detector.

25. The method of claim 24, wherein the one or more metrology measurements comprise:
at least one of a thickness measurement of a film on the object, a composition measurement of a film on the object, a refractive index measurement of at least a portion of the object, an overlay measurement between multiple layers on the object, or a dimension measurement of a feature on the object.

* * * * *